US005713916A

United States Patent [19]

Dias

[11] Patent Number: 5,713,916

[45] Date of Patent: Feb. 3, 1998

[54] METHOD AND SYSTEM FOR COUPLING ACOUSTIC ENERGY USING SHEAR WAVES

[75] Inventor: J. Fleming Dias, Palo Alto, Calif.

[73] Assignee: Hewlett Packard Company, Palo Alto, Calif.

[21] Appl. No.: 608,225

[22] Filed: Feb. 28, 1996

[51] Int. Cl.$^6$ .......... A61B 17/32

[52] U.S. Cl. .......... 606/69; 128/663.01; 604/22

[58] Field of Search .......... 73/632, 642; 310/333, 310/334, 536, 325; 606/1, 128, 159, 169; 604/22; 128/662.05, 663.01, 662.06

[56] References Cited

U.S. PATENT DOCUMENTS

| | | | |
|---|---|---|---|
| 2,549,891 | 4/1951 | Carlin | 73/632 |
| 2,702,472 | 2/1955 | Rabinow | 73/632 |
| 4,870,953 | 10/1989 | DonMichael et al. | 128/24 |
| 4,887,606 | 12/1989 | Yock et al. | 128/662.05 |
| 5,159,226 | 10/1992 | Montgomery | 310/333 |
| 5,209,719 | 5/1993 | Baruch et al. | 604/22 |
| 5,262,969 | 11/1993 | Culp | 310/333 |
| 5,269,297 | 12/1993 | Weng et al. | 128/24 |
| 5,304,115 | 4/1994 | Russell et al. | 604/22 |
| 5,306,980 | 4/1994 | Montgomery | 310/333 |
| 5,326,342 | 7/1994 | Pfluege et al. | 604/22 |
| 5,342,292 | 8/1994 | Nita et al. | 604/22 |
| 5,368,557 | 11/1994 | Nita et al. | 604/22 |
| 5,368,558 | 11/1994 | Nita | 604/22 |
| 5,376,858 | 12/1994 | Imabayashi et al. | 310/333 |
| 5,380,274 | 1/1995 | Nita | 604/22 |
| 5,390,678 | 2/1995 | Gesswein et al. | 128/662.06 |
| 5,394,874 | 3/1995 | Forestieri et al. | 128/5 |
| 5,397,293 | 3/1995 | Alliger et al. | 601/2 |
| 5,397,301 | 3/1995 | Pflueger et al. | 604/22 |
| 5,417,672 | 5/1995 | Nita et al. | 604/283 |
| 5,427,118 | 6/1995 | Nita et al. | 128/772 |
| 5,476,011 | 12/1995 | Cornforth | 73/634 |

FOREIGN PATENT DOCUMENTS

WO 92/11815 7/1992 WIPO .

OTHER PUBLICATIONS

I. L. Gelles, (1969) "Optical-Fiber Ultrasonic Delay Lines", *J. of the Acoustical Society of America*, 39(6), pp. 1111–1119.

A. J. DeVries et al. (1971) "Characteristics of Surface-Wave Integratable (SWIFS)", *IEEE Transactions on Broadcast and Television Receivers* BTR-17(1), pp. 16–23.

J. Fleming Dias, (1981) "Physical Sensors Using SAW Devices", *Hewlett-Packard Journal*, pp. 18–20.

W. W. Hansen et al. (1988) "A New Principle in Directional Antenna Design", *Proceedings of the Inst. of Radio Engineers*, 26(3), pp. 333–345.

J. D. Kraus (1988) Electromagnetics, 4th ed, "Antennas and Radiation", McGraw-Hill pp. 716–785.

J. Fleming Dias (1994) Electronic Instrument Handbook, 2nd ed., "Transducers", McGraw-Hill pp. 5.1–5.50.

*Primary Examiner*—Michael Buiz
*Assistant Examiner*—Patrick W. Rasche
*Attorney, Agent, or Firm*—Marc P. Schuyler

[57] ABSTRACT

A system and method for coupling acoustic energy within a waveguide provides highly efficient and sensitive acoustic energy generation and detection. In particular, an ultrasound angioplasty system is described which makes use of an end-fire array of ring transducers to produce highly directionalized sound within an acoustic waveguide. The transducers can be made circularly symmetric, and may be composed of multiple segments for generating sound waves in independent x and y spatial modes within the acoustic waveguide. Each ring transducer is optimally spaced $\frac{1}{2}\lambda_L$ from its neighbor transducers, such that alternate transducers transduce 180-degrees out of phase, and may have their electrical end inverted for common drive, or for summing of transducer electrical outputs when the array is used as a detector. The phased array may also be used in a resonant acoustic energy system used to detect pressure variations or reflections from a substance, for example, for detecting the progress of chemical reactions, liquid level sensing, etc., imaging, or in various other ultrasound applications.

19 Claims, 5 Drawing Sheets

METHOD AND SYSTEM FOR COUPLING ACOUSTIC ENERGY USING SHEAR WAVES

The present invention relates to a method and system for coupling acoustic energy.

BACKGROUND

An acoustic energy transmission system typically transmits sound waves to some distant point, where mechanical energy is derived from the sound and used in an application. The sound waves can be generated using any of a number of conventional transducers, for example, audio speakers and piezoelectric devices. These devices are caused to vibrate back and forth to convert electrical energy to movements of air; they can also sometimes be used in the reverse sense, to convert movements of air to electric charge. In traditional usage, these devices are coupled to a voltage generator and they responsively transmit longitudinal waves through the air, that is, the air is moved back and forth in the same direction in which the sound waves travel.

One example of an acoustic energy transmission system is an ultrasound angioplasty system. In this type of system, ultrasound is used to clear blocked or partially blocked human arteries. The ultrasound can be generated by an ultrasound generator, and coupled via an encased solid wire through a catheter probe positioned within the occluded artery. The ultrasound wire causes an extendable catheter tip to vibrate, thereby disintegrating arterial plaque that the extendable member contacts. To best perform this task, it is necessary to have strong ultrasound waves arrive at the catheter tip. Unfortunately, use of a solid wire makes it difficult to efficiently couple acoustic energy into the solid wire and have strong ultrasound arrive at the catheter tip. The solid wire is also a relatively expensive, not easily-replaced part of the system. However, solid wires are generally used in ultrasound angioplasty, since the solid wires facilitate probe vibration in two or more spatial dimensions, which is desired for best clearing arterial plaque.

In general, acoustic energy transmission systems such as these suffer from several limitations. First, the use of a transducer to create longitudinal sound waves typically requires that the transducer have a moving surface which is perpendicular to, and directly in the path of, a waveguide, e.g., the transducer's vibrating surface moves back and forth toward and away from the waveguide along the transmission direction. This requirement renders it difficult to channel sound from multiple longitudinal wave transducers into a single waveguide in a reinforcing manner. Also, this requirement makes it difficult to generate directional acoustic energy, e.g., sound that travels substantially only in a single direction without losing substantial energy via dispersion. Many acoustic energy systems therefore generally feature undesired loss of power, caused by loss of acoustic energy through walls of the waveguide.

It is desired in many acoustic energy systems to have as little loss as possible through the waveguide, and to produce a very strong signal at the distant end of a transmission path. In the example of the ultrasound angioplasty system just given, this would enable very strong high frequency vibrations to be produced at a catheter tip inside a human body, using a relatively inexpensive and efficient sound generator. In the case of other ultrasound systems, for example, imaging systems and various acoustic sensors, it is also desired to have a system that detects weak sound signals with heightened sensitivity.

A definite need exists for an improved acoustic energy system that couples acoustic power through a waveguide with relatively little propagation loss, and which can produce and maintain intense ultrasonic waves throughout the waveguide. Further still, a need exists for a system that can produce complex wave patterns. In the context of an ultrasound angioplasty system, such a system would be beneficial in permitting a catheter probe to perform complex motions, enhancing the unblocking process. The usefulness of such a system would not just be limited to ultrasound angioplasty, but rather, would have applicability to other fields that use acoustic energy transmission, including measurement and computation systems. The present invention solves the aforementioned needs and provides further, related advantages.

SUMMARY OF THE INVENTION

The present invention provides a highly efficient method and system for coupling acoustic energy to a waveguide using at least one shear wave transducer. In particular, the present invention uses a shear wave transducer that transduces shear waves propagating perpendicular to the waveguide, towards and away from its center where a "sweet spot" is created in the waveguide. As a result, the waveguide need not physically be obstructed by a transducer, as in the case of some devices that utilize longitudinal wave transducer. The present invention thereby facilitates use of the transducer either as a generator or detector in systems where it is advantageous to have the acoustic transducer not substantially impede longitudinal waves.

For example, in one aspect of the invention, a phased-array of shear wave transducers can be used as part of an ultrasound angioplasty device, to generate intense shear waves that are efficiently coupled to the waveguide and transmitted as longitudinal waves to an ultrasound catheter. In this manner, all of the transducers independently generate longitudinal waves that reinforce each other as they travel along the center axis of the waveguide.

In another aspect of the invention, the shear wave transducer and waveguide can be used to form an acoustic detector, with the shear wave transducer detecting longitudinal waves and responsively producing an output signal which matches a predetermined frequency. Using multiple transducers, a phased array can be created which is highly tuned to longitudinal waves of a particular frequency.

A more particular aspect of the invention provides a shear wave transducer which is a ring, or annular, transducer. The ring transducer can be coupled to an oscillation source and used to generate shear waves and direct them radially inward to converge at a "sweet spot" of a waveguide. As a result, longitudinal waves can be generated within the waveguide and transmitted to a distal point. By using many shear wave transducers arranged along the waveguide to form a phased array, very intense longitudinal waves can be generated within and transmitted efficiently by the waveguide. A shear wave transducer can, applying the principles of the present invention, be made of different pairs of transducer segments which are driven by different excitation sources, to simultaneously produce different waves within the waveguide. For example, this aspect of the invention can be used to create complex motions in an extendable member of an ultrasound catheter.

The invention may be better understood by referring to the following detailed description, which should be read in conjunction with the accompanying drawings. The detailed description of a particular preferred embodiment, set out below to enable one to build and use one particular implementation of the invention, is not intended to limit the enumerated claims, but to serve as a particular example thereof.

BRIEF DESCRIPTION OF THE DRAWINGS

FIG. 2 shows sideways particle motion of shear waves which are propagating radially inward (as indicated by the reference arrows in FIG. 1). Convergence of the shear waves at the "sweet spot" causes intense particle motion along the center axis of the waveguide at the "sweet spot," such that longitudinal waves are transmitted along the waveguide. An arrow within the transducer at the two locations indicates a poling vector of the transducer.

FIG. 7 shows propagation of shear waves in a radially inward manner, as indicated by various reference arrows appearing in FIG. 7.

FIG. 8 shows a detector which is tuned to provide an electronic output in response to the strength of acoustic energy at the predetermined ultrasound frequency.

FIG. 11 shows use of two phased arrays of ring transducers, as a sound generator and a detector, respectively.

FIG. 12 shows a block of PZT material that will be cored to remove a cylindrical section of PZT material (indicated in phantom); an original poling vector of the PZT material is indicated for purposes of illustration, which may or may not preexist in a given PZT sample.

FIG. 13 shows the cylindrical section of FIG. 12 removed from the PZT block, and how the cylindrical section is sliced along the height of the cylindrical shape to create multiple ring transducers; in addition, a core which will be removed to form the ring geometry is indicated in phantom.

FIG. 14 indicates deposition of metal electrodes on opposite lateral sides of a ring from FIG. 13. The electrodes are coupled to a high voltage, to set a poling vector which is normal to the ring (i.e., parallel to the direction of the ring's lateral thickness).

FIG. 15 shows the ring from FIG. 14, where the metal electrodes are removed and new peripheral excitation electrodes are deposited.

FIG. 16 is a cross-sectional diagram showing simultaneous vacuum-chamber deposition of electrodes on radially inward and outward peripheries of multiple ring transducers.

FIG. 17 is a cross-sectional diagram showing one ring transducer of FIG. 16, installed on an acoustic waveguide (in phantom), and the various electrical connections associated therewith.

DETAILED DESCRIPTION

The invention summarized above and defined by the enumerated claims may be better understood by referring to the following detailed description, which should be read in conjunction with the accompanying drawings. This detailed description of several particular preferred embodiments, set out below to enable one to build and use certain implementations of the invention, is not intended to limit the enumerated claims, but to provide particular examples thereof. The particular examples set out below are the preferred implementation of devices for coupling acoustic energy, for example, an ultrasound generator and an ultrasound detector. The invention, however, may also be applied to other types of systems as well.

Figure 1:
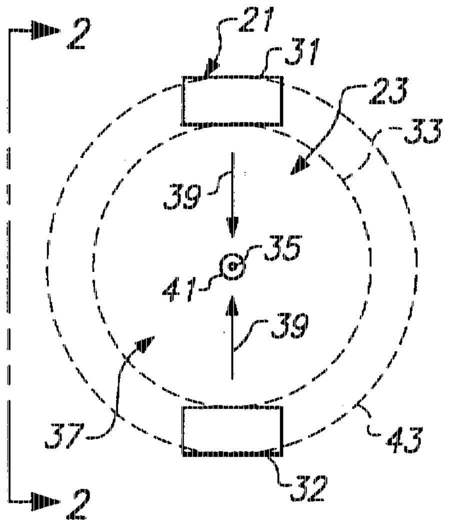
FIG. 1 is a cross-section of a shear wave transducer that overlies at least two locations around a waveguide; shear waves produced at each location converge within the waveguide to form a "sweet spot," which is seen at the center of FIG. 1.
Figure 2:
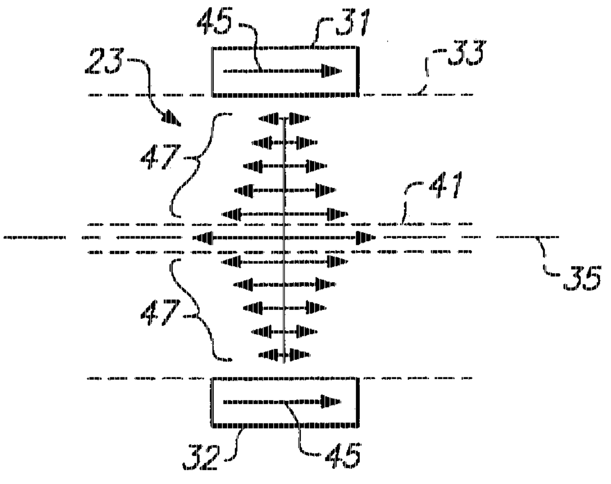
FIG. 2 is a side view of the transducer and waveguide of FIG. 1, taken along line 2—2 of FIG. 1.
Figure 3:
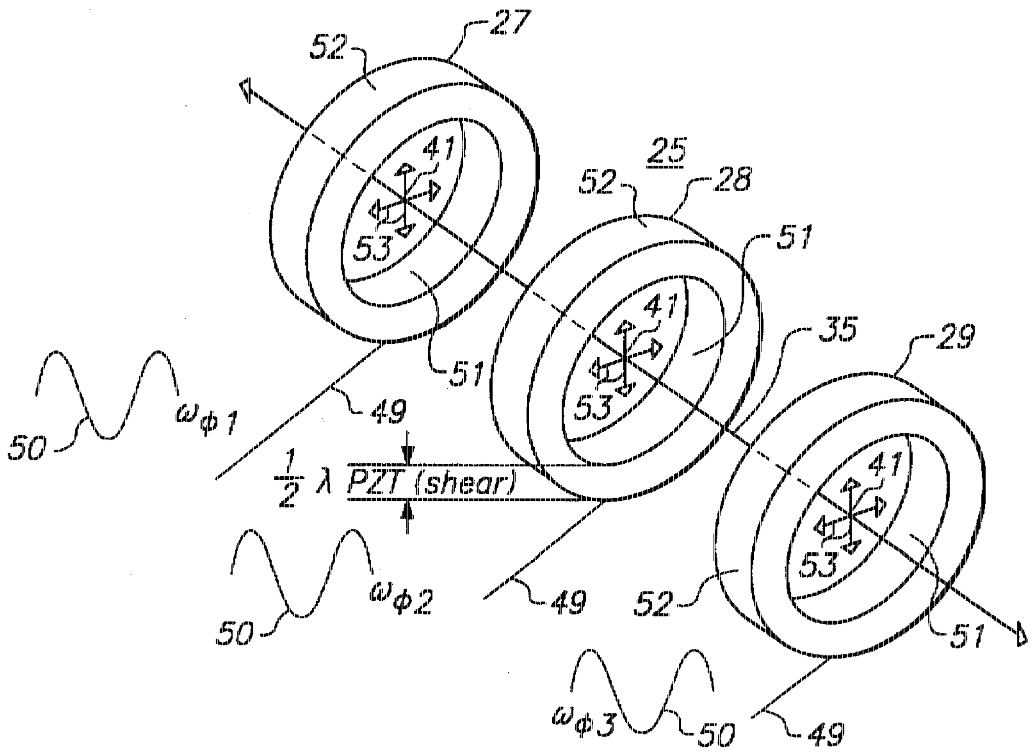
FIG. 3 is an illustrative diagram of a phased array of ring transducers used to reinforce very intense axially propagating longitudinal waves within the waveguide.

I. Introduction To The Transducer Elements And End Fire Array Used In The Preferred Embodiments FIGS. 1–3 are used to illustrate basic principles of the present invention. In particular, FIGS. 1–2 show use of a shear-wave transducer 21 to transduce acoustic energy without interfering with the passage of longitudinal waves which are traveling along a waveguide 23. FIG. 3 shows an end-fire array 25 of multiple transducers 27, 28, 29 which combine to efficiently transduce intense acoustic energy, either generating acoustic energy or, alternatively, detecting it in the waveguide.

FIG. 1 shows a general case where the shear wave transducer 21 has two discrete segments 31 and 32 that lie about a periphery 33 of a waveguide 23. The waveguide 23 may be circular in cross-section, as seen in phantom lines of FIG. 1, or it may be any other shape. The waveguide 23 has a transmission axis (or waveguide axis) 35 along which it is desired to transmit acoustic energy, for example, ultrasound; the waveguide axis 35 appears as a dot in FIG. 1, and is normal to FIG. 1, extending into and out of the paper on which FIG. 1 is drawn.

The shear wave transducer 21 can be used either as an acoustic energy generator, in which case electrical signals cause the transducer to generate shear waves and direct them toward a middle area 37 of the waveguide (as indicated by the reference arrows 39) or, alternatively, as an acoustic detector, in which case shear waves travel in the reverse sense. For purposes of this introductory section, it will be assumed that the transducer 21 is being used as an acoustic energy generator.

The transducer 21 is structured to direct identical shear waves in a converging manner, toward a "sweet spot" 41 of the waveguide. In this regard, "shear waves" are waves that cause particle motion perpendicular to the waves' direction of travel, like deep water ocean waves. "Longitudinal waves," by contrast, cause particle motion along the direction of travel. As seen in FIG. 1, the reference arrows 39 indicate the direction of shear wave propagation, which is perpendicular to the direction of particle motion (the latter occurring in a direction normal to FIG. 1, into and out of the paper upon which FIG. 1 is drawn). In this manner, as the shear waves converge, particle motion becomes more intense, and is most intense at the "sweet spot" 41. While FIG. 1 shows a general case where only two discrete transducer segments 31 and 32 are used, more segments may be used, for example, around a circular waveguide, in which case particle motion at the "sweet spot" is even further enhanced. As indicated by an outer circle 43 of FIG. 1, the transducer 21 may be made continuous around the waveguide 23, as with a ring transducer, in which case particle motion will be even more intense.

FIG. 2 shows in cross-section the transducer 21 and waveguide 23 of FIG. 1, taken from a vantage point identified by line 2—2 of FIG. 1. In particular, the two discrete transducer segments 31 and 32 are seen to have a poling vector 45, which indicates direction of particle motion when the transducer 21 is excited by an electrical signal. Back-and-forth particle motion is indicated by the various arrows 47 and, as illustrated in FIG. 2, the motion becomes more intense closer to the "sweet spot" 41. As seen in FIG. 2, the "sweet spot" 41 extends longitudinally along the waveguide 23, approximately at the waveguide's transmission axis 35.

FIG. 3 shows the end-fire array 25 of several shear wave ring transducers 27, 28, 29 which are configured to either sense or generate ultrasound optimally having a predetermined frequency. Configuration of the array 25 is also briefly introduced here in the context of an ultrasound generator, before a discussion of ultrasound angioplasty and measurement system embodiments of the present invention. Additional details of the construction of the array 25 and its use as an ultrasound detector will also be provided further below.

Each ring transducer 27, 28, 29 has a dedicated set of electronic leads 49 which supply the transducer with a sinusoidal signal 50 and cause the transducer to responsively vibrate and generate ultrasound. Each transducer 27, 28, 29 is specially constructed to generate shear waves of ultrasound which are directed radially inward, toward the center of the ring shape of each transducer. To this effect, each transducer is made from specially-processed piezoelectric material (PZT) and is formed to have (1) a radial thickness of $\frac{1}{2}\lambda_{PZT}$ (where $\lambda_{PZT}$ corresponds to the shear wave velocity $V_s$ in the PZT material), (2) electrodes of opposite polarity 51 and 52 existing on radial edges of the ring geometry, and (3) poling which is perpendicular to the ring geometry (i.e., parallel to the axis 35). The innermost radial electrode 51 of each transducer is optimally used as a ground electrode, while the outermost electrode 52 of the transducers are driven by the sinusoidal signal. The sinusoidal signal 50 as it is imparted to the outermost electrodes 52 is generated by an excitation source, and is described by a frequency ω and a variable phase lag ϕ. All of the transducers 27, 28, 29 receive a proper phase lag with respect to their spacings apart, such that they each reinforce intense longitudinal ultrasound waves that are propagated along the waveguide axis 35, which is a common center axis of all of the transducers. Thus, in the preferred case where ten ring transducers are used, intense, highly-directional longitudinal waves can be generated along the waveguide axis 35. This configuration provides for highly efficient acoustic coupling, particularly in applications such as ultrasound angioplasty, wherein the waveguide 23 is a solid metal wire.

Preferably, each transducer (transducer 28, for example) is spaced $\frac{1}{2}\lambda_L$ from its neighbor transducers 29 and 29 (where $\lambda_L$ depends upon the longitudinal ultrasound velocity $V_L$ in the transmission media, i.e., in the waveguide material); this configuration is particularly desirable, since 180-degree opposite phases of an oscillation signal are readily derived from a phase splitter or push-pull driver, such as a center tap transformer. However, other phasings and spacings between the transducers of the array 25 are possible, as will be apparent to those of ordinary skill in the art.

Figure 4:
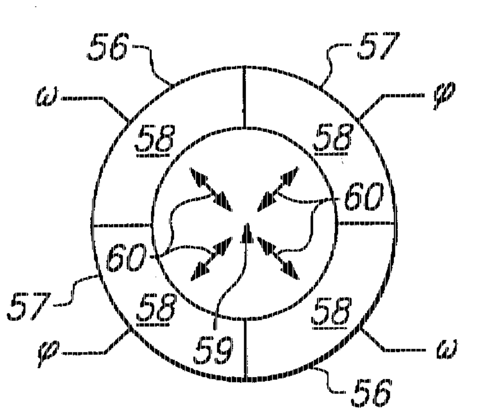
FIG. 4 shows an alternative embodiment of the ring transducer of FIG. 3. In particular, the transducer of FIG. 4 includes two pairs of transducer segments, each pair driven by an oscillation signal ω and ϕ, respectively.

The shear wave transducers do not necessarily have to be shaped as continuous rings. For example, FIG. 4 shows a transducer 55 having two distinct transducer segment pairs 56 and 57, each having two opposing segments 58. Each pair 56 and 57 receives an oscillation signal ω or ϕ (of different frequency) and propagates shear waves radially-inward toward a center 59 of the waveguide, as indicated by reference arrows 60. Notably, the location of the "sweet spot" (or perhaps plural "sweet spots") for the transducer of FIG. 4 depends upon the arrangement of the pairs 56 and 57 and any relative phase lag imparted to oscillation signal ω or ϕ within each pair.

Figure 5:
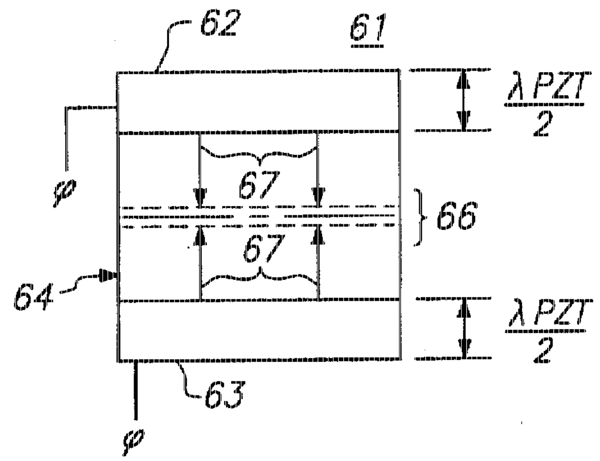
FIG. 5 shows an alternative, square shaped transducer, used with a waveguide which is rectangular in cross-section.

FIG. 5 shows a transducer 61 that has two opposing flat segments 62 and 63 which bracket a rectangular waveguide 64. In this configuration, shear waves are directed to a middle plane 65 of the waveguide, as indicated by reference arrows 67, with a planar "sweet spot" 66 being formed throughout the middle of the waveguide.

As will be seen from this introduction therefore, an end fire array of shear wave transducers can be used to produce highly-directional ultrasound that propagates intensely along a waveguide axis 35. As discussed further below, the end fire array 25 can also be used as a highly-sensitive, frequency specific detector, in which case the electric leads 49 provide electronic outputs from each of the transducers.

II. The End Fire Array Used As An Acoustic Generator

Figure 6:
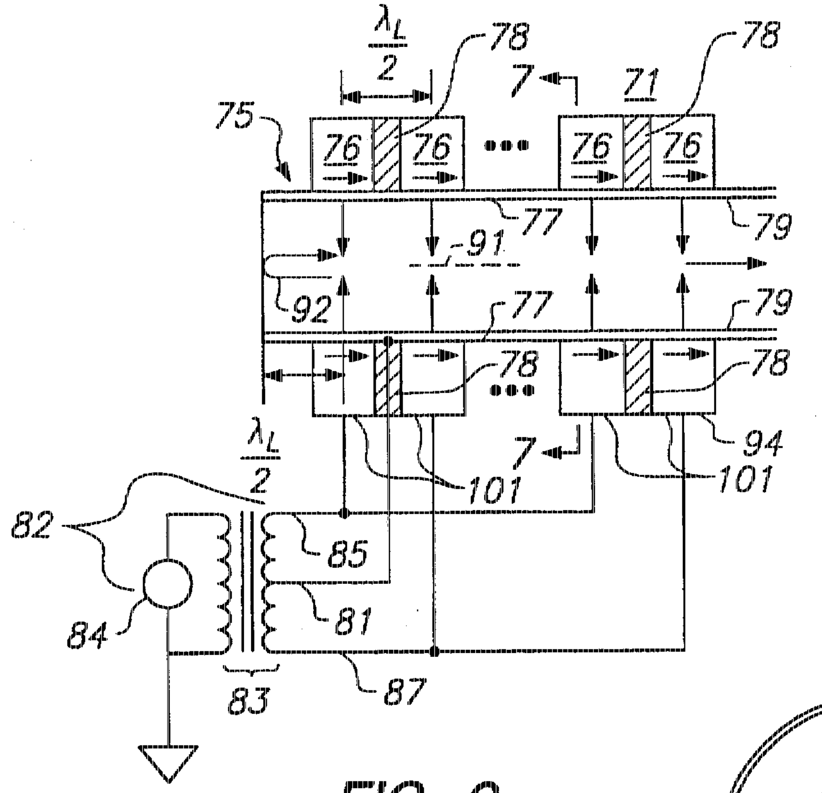
FIG. 6 is a diametrical cross-section of an ultrasound generator and an acoustic waveguide of the present invention. Ultrasound is produced by each of ten ring-shaped shear wave transducers, such that intense longitudinal ultrasound waves are transmitted through the acoustic waveguide, in the direction indicated by a reference arrow at the right side of FIG. 6.

FIG. 6 provides a cross-section of the ultrasound generator 71, which couples sound to an acoustic waveguide 73. In particular, a first end 75 of the waveguide 73 is fitted with ten ring transducers 76 which are bonded with an epoxy to a circular periphery 77 of the waveguide. At this first end 75, the waveguide is also coated with a conductive material 79 (preferably a gold-based mixture is used, although any thin film conductive material can be used which adheres well to the waveguide), the conductive material being connected to a center tap connection 81 (i.e., ground) of a transformer 83. It is this transformer 83, and an oscillator 84, which together form the excitation source 82 that generates the push-pull oscillation signal.

Each of the ring transducers is spaced apart from its neighbor transducers at intervals of $\frac{1}{2}\lambda_L$, the ring transducers being separated by Teflon spacer rings that rigidly maintain the spacing between adjacent transducers. The transducers are excited by opposite power phases provided by end-taps 85 and 87 of the transformer. The opposite power phases provided by the transformer are alternately coupled to outermost radial transducer electrodes 101. As a result, the ten ring transducers 76 generate longitudinal waves that are highly-directional within the acoustic waveguide in both directions along a transmission axis 91 of the waveguide, as indicated by arrows 92 and 93. However, the first end 75 of the waveguide 73 is terminated with a polished face 89 at a distance of $\frac{1}{4}\lambda_L$ from a first one of the transducers, such that longitudinal waves emerging from the transducers toward the left side of FIG. 6 (as indicated by reference arrow 92) are reflected back along the transmission axis 91. These reflected waves help reinforce production of longitudinal waves directed toward a distant, second end of the waveguide, as indicated by the reference arrow 93 in FIG. 6.

Figure 7:
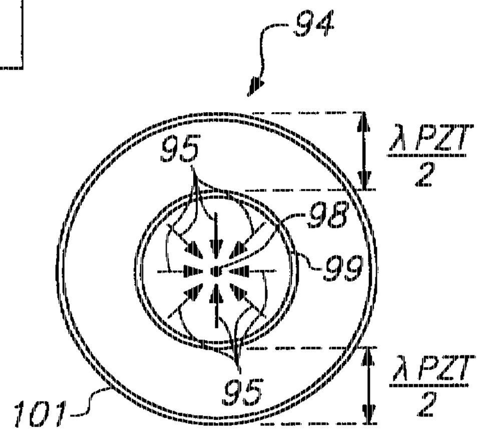
FIG. 7 is a cross-section of one ring transducer and the acoustic waveguide, taken along lines 7—7 of FIG. 6.

FIG. 7 is a cross sectional view of a single ring transducer 94, taken across lines 7—7 of FIG. 6. Several arrows 95 indicate the direction of propagation of shear waves generated by the ring transducer 94 toward the center of the waveguide (i.e., the transmission axis, which appears as a point 98 in FIG. 7). Particle movement for the shear waves occurs in a direction perpendicular to FIG. 7, into and out of the drawing (and along the transmission axis, which is designated in FIG. 6 by the reference numeral 91). Since shear waves converge at the center point 98, particle movement is strongest at that point. Preferably, the diameter of the acoustic waveguide is such that the waveguide supports only a single mode of wave propagation, to best maintain the strength of particle movement.

FIG. 7 also illustrates innermost and outermost electrodes 99 and 101 of the transducer 94. As mentioned earlier, each transducer is composed of a piezoelectric material which is poled in a manner to generate shear waves. The electrodes 99 and 101 are non-conventional in the sense that they are added to the radial edges of the ring transducers, with the outermost electrode 101 preferably coupling a signal having a particular phase to the transducer, and the innermost electrode 99 providing a common ground for each transducer. Importantly, each transducer has a radial thickness of $\frac{1}{2}\lambda_{PZT}$ ($\lambda_{PZT}$=t$V_{PZT}$, where $V_{PZT}$ is the shear wave velocity in the PZT material) such that it is configured to optimally generate waves having frequency $\omega=v_{PZT}/\lambda_{PZT}$ (e.g., a few centimeters) when coupled to an oscillation signal of the same frequency. An inner bore of the transducer is made to correspond closely to a diameter of the waveguide 73 such that, during assembly, each transducer may be snugly fitted over the acoustic waveguide and adhered thereto, if necessary, using a conductive adhesive.

III. The End Fire Array Used As Acoustic Detector

Figure 8:
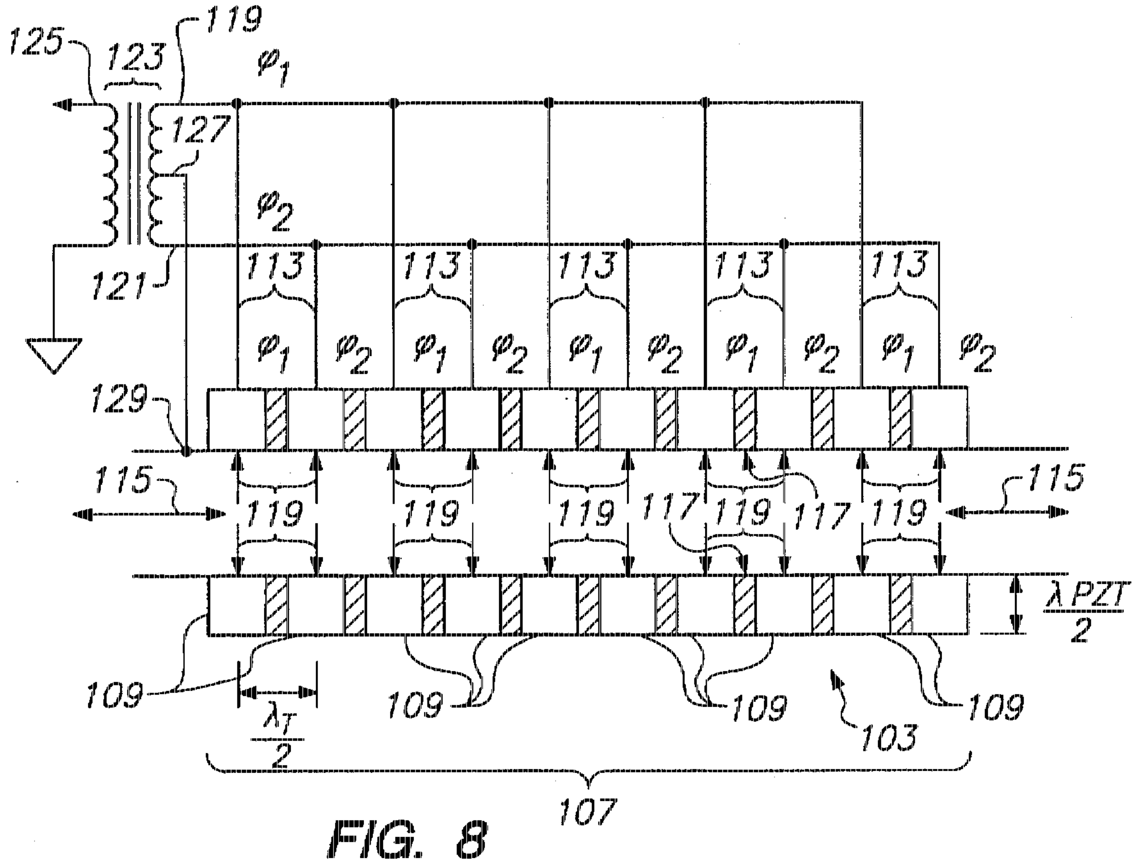
FIG. 8 shows an ultrasound detector which embodies the principles of the present invention. In particular.

FIG. 8 illustrates an acoustic detector 103. In particular, the detector also includes an end fire array 107 composed of ten ring transducers 109 which are mounted to the periphery of an acoustic waveguide 111. Each transducer 109 is spaced apart by $\frac{1}{2}\lambda_L$, and produces an electronic output on signal leads 113 which represents contribution to acoustic energy within the waveguide at a predetermined frequency $\omega$ (which is that frequency which matches the characteristics of the end fire array in terms of transducer thickness, etc., as has been previously described). Longitudinal acoustic waves traveling along the waveguide are indicated by the reference arrows 115. These waves will be dampened somewhat near the periphery 117 of the waveguide, giving rise to shear waves which diverge radially from the center of the waveguide and toward the transducers, as indicated by the reference arrows 119 of FIG. 8. Vibrations are thereby imparted to the PZT material of each transducer 109, causing each transducer to generate an electronic signal having frequency $\omega$ (where $\omega=v_L/\lambda_L$, $v_L$ being longitudinal wave velocity in the transmission media). Since each transducer is spaced apart by $\frac{1}{2}\lambda_L$, every other transducer will be 180-degrees out of phase (providing output signals $\phi_1$ and $\phi_2$ of FIG. 8). Accordingly, each transducer's output signal $\phi_1$ or $\phi_2$ may be passed conveniently to alternate taps 119 or 121 of a center tap transformer 123, and used to generate an array output signal 125 having frequency $\omega$. As before, a center tap 127 of the transformer 123 is connected to a peripheral conductor 129 of the waveguide 111 to provide a ground for all transducers.

The array output signal 125 can be utilized in a wide variety of applications where it is desired to have an acoustic detector which is highly tuned to specific frequencies, for example, in various measurement systems. For example, as will be explained further below, the array output signal 125 can be coupled to electronics and a visual display (not seen in FIG. 8) used to indicate to a user a characteristic of detected acoustic waves. The visual display could be used, for example, to display distance to a detected object, pressure as it affects a special waveguide, or molecular structure as a chemical reaction proceeds.

IV. Application To Ultrasound Angioplasty

The preferred application of the invention is in the field of ultrasound angioplasty. In practice, a patient's bloodstream is injected with a dye, which gives rise to a strong visual contrast on a video angiogram display. This display (not shown in the accompanying figures) relies on x-ray fluoroscopy to display and highlight the occluded blood vessel segment, blood vessel walls and, preferably also, a catheter as it is being advanced through the blood vessel to a stenosed portion of the blood vessel. Using such a visual display facilitates use of ultrasound angioplasty without the need for bypass surgery.

Figure 9:
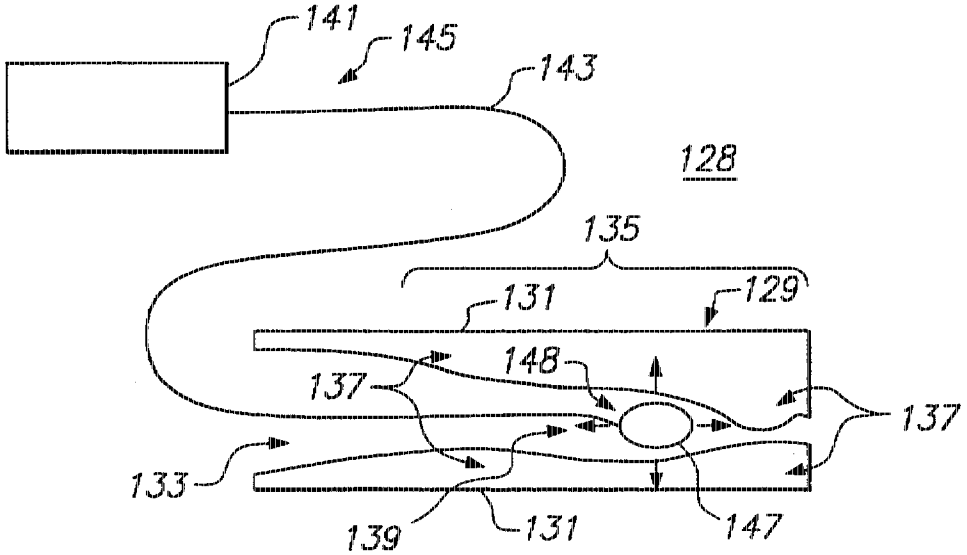
FIG. 9 is a schematic diagram used to explain the general parts of an ultrasound angioplasty system, one application of the present invention.
Figure 10:
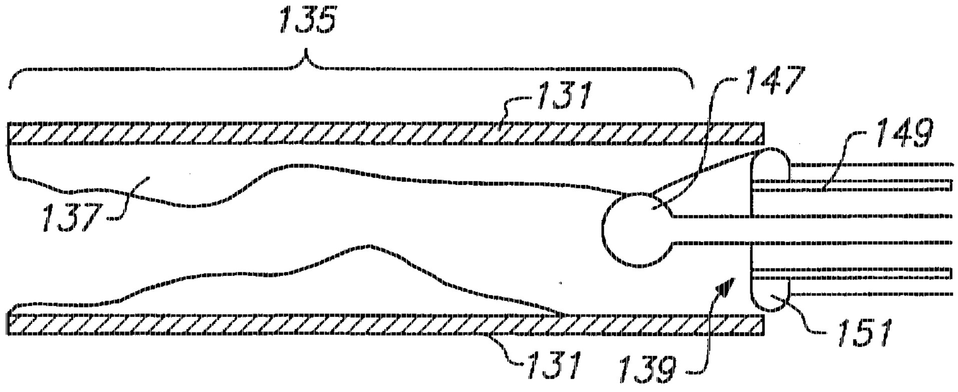
FIG. 10 is an illustrative diagram of an ultrasound catheter and probe used in the system of FIG. 9.

FIGS. 9 and 10 illustrate an ultrasound angioplasty device 128. In particular, FIG. 9 shows a schematic view of the device being used to clear a human artery 129. Walls 131 of the artery define a passageway 133, which at a stenosed portion 135 of the artery seen in FIG. 9 is obstructed by arterial plaque 137. To remove the plaque 137 as part of the angioplasty procedure, the angioplasty device 128 makes use of an ultrasound catheter 139, which receives ultrasound from an ultrasound generator 141 located outside the patient's body. The ultrasound generator 141 is preferably configured as described above, with reference to FIGS. 6 and 7, such that intense ultrasound waves are efficiently coupled to the ultrasonic catheter 139. Ultrasound produced by the generator 141 is conveyed by an acoustic waveguide 143 which is composed of a nickel-titanium material which is flexible and transmits ultrasound very well. Ultrasound waves are generated at a first end 145 of the waveguide 143, as has been previously described, and is conveyed within the to an extendable, bulbous termination 147 of the catheter (at a second 148 of the waveguide). As alluded to earlier, the ultrasound generator 141 preferably makes use of an end fire array of ten ring-shaped shear wave transducers, mounted about a periphery of the first end 145 of the waveguide.

The ultrasound catheter 139 is shown in FIG. 10, and it includes an outer sheath 149 which houses the extendable termination 147 until the catheter has been advanced to the stenosed portion 135 of the artery. At that point in time, a balloon device 151 of the sheath or equivalent mechanism is selectively used to lock the catheter in place with the walls 131 of the artery, and the extendable member is then moved from the sheath toward the stenosed portion 135. The ultrasound generator 141 may then be activated to cause the termination 147 to vibrate. The catheter 139 may be a triple lumen catheter, and may include additional tubes which supply and extract fluid from the stenosed portion, for the purpose of removing plaque splinters which are lifted from the artery walls by the probe.

There are many ultrasound catheters which can be used as part of the ultrasound angioplasty device 127 disclosed herein. Selection of a suitable ultrasound catheter is left to discretion of one or ordinary skill, and examples of suitable catheter design may be observed, for example, in U.S. Pat. Nos. 4,870,953, 5,209,719, 5,269,297 and 5,304,115, and International Publication Number WO 92/11815 which are hereby incorporated by reference.

V. Application To A Resonant Measurement System

Figure 11:
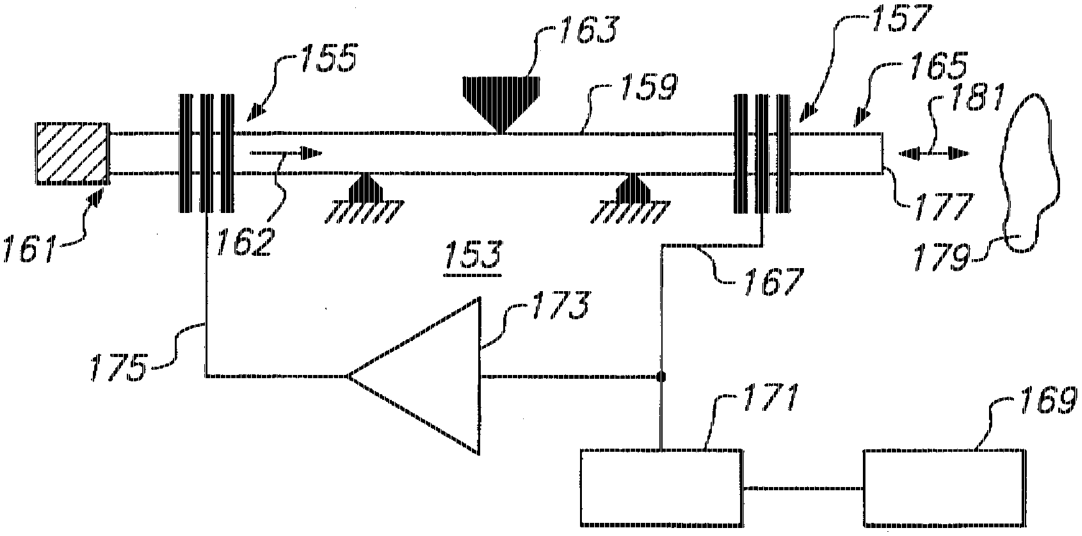
FIG. 11 is a schematic diagram of a resonant measurement system.

FIG. 11 shows an embodiment of the present invention which is used for measurement of physical conditions, or alternatively, as a detector of reflected ultrasound. In this resonant acoustic system 153, two phased arrays are utilized, including one array 155 used as an acoustic generator (such as illustrated by FIG. 6), and a second array 157 as acoustic detector (such as illustrated by FIG. 8). The system 153 does not directly use a source of electric power to generate ultrasound, but rather relies upon background noise and electronic amplification by amplifier 173 to create a resonant condition in a waveguide 159.

A first end 161 of the waveguide is closed, and helps reinforce production of longitudinal waves by the ultrasound generator, as indicated by the directional arrow 162. If the waveguide 159 is used to measure ambient physical conditions, for example pressure or temperature, the waveguide is exposed to these conditions at a location in-between the generator 155 and the detector 157, for example, by direct exposure. An arrow 163 is used in FIG. 11 to indicate application of pressure to the waveguide 159, for example, for detecting pressure within a vacuum chamber. The pressure causes the waveguide to bend, thereby increasing or decreasing path length from ambient conditions, which correspondingly affects the phase of the acoustic wave detected by the acoustic detector 155. The phase change causes a proportional change of the resonant oscillation frequency. In this system, a second end 165 of the waveguide proximate to the detector may be closed in a manner to constructively reflect waves at the particular frequency the detector is tuned to.

The acoustic detector 157 utilizes electric leads to provide an array output in the manner described above in connection with FIG. 8. The individual transducers generate electric output signals (indicated in FIG. 8 as either $\phi_1$ or $\phi_2$) that are retarded by an appropriate phase and then summed together to generate an array output 167 of the detector's phased array that collectively represents strength of detected acoustic energy. This array output 167 may then be processed and visually displayed, such as by a meter or a display 169 seen in FIG. 11, in connection with processing electronics 171. In addition, the array output 167 is also passed through a gain device 173 and used to generate an oscillation signal 175 that drives the acoustic generator 155. In this instance, the excitation source for the acoustic generator includes the gain device 173 and the array output 167 provided by the acoustic detector 157. The oscillation signal 175 is provided to each of ten transducer rings of the acoustic generator 155 (with appropriate phase lags) to generate ultrasound and help create the resonant condition.

As an alternative, the resonant acoustic system 153 just described can also be used to detect surfaces, such as specific textures or liquid level, for example. In this instance, the waveguide seen in FIG. 11 is not terminated at the second end 165, but rather, directs acoustic waves from an opening 177 and toward a target 179 that is to be measured. Acoustic waves are reflected back from the target to the waveguide (as indicated by arrow 181) and constructively or destructively combine with the acoustic waves to change acoustic energy detected by the acoustic detector. The processing electronics 171 are appropriately configured to provide the desired monitoring of measurement conditions to the user.

Those desiring additional information regarding the use of an ultrasound system as just described can be obtained from the article "Physical Sensors Using SAW Devices," by J. Fleming Dias, which appeared in the Hewlett-Packard Journal, December 1981, which is hereby incorporated by reference.

VI. Fabrication Of The Transducers And End Fire Array

The fabrication of the transducers used in the end fire array will be explained with reference to FIGS. 12–17.

Figure 12:
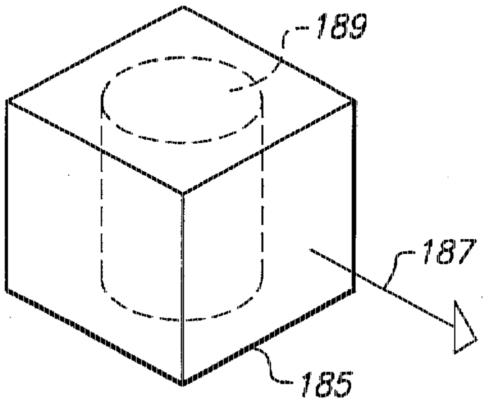
Figure 13:
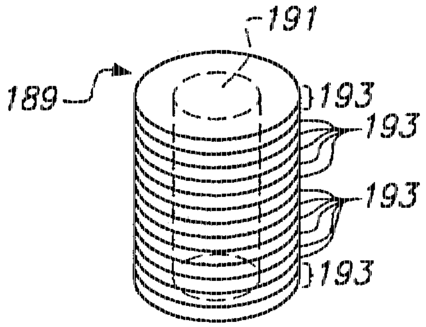

Individual transducers are cut from a block 185 of piezoelectric material (PZT), which may have a poling vector 187 as seen in FIG. 12. A diamond core drill is utilized for this purpose, to core the PZT block 185 and remove a center cylindrical section 189 from the block. As seen in FIG. 13, the cylindrical section 189 is then again cored along its height dimension, to form a bore 191 in the cylindrical section using a ceramic lathe. The outer diameter of the cylindrical section is then adjusted to match the appropriate design thickness for the transducer rings. Following that procedure, a diamond saw is then used to slice the cylindrical section 189 perpendicular to the height dimension to form individual rings 193. These annular rings are parallel lapped to a common thickness to prevent generation of spurious acoustic modes. The individual rings 193 may have an unknown poling vector at this point in the process, which must be correctly set for the rings to correctly operate as shear wave transducers.

Figure 14:
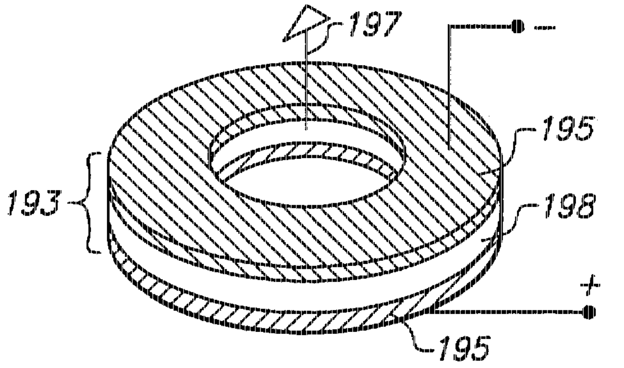
Figure 15:
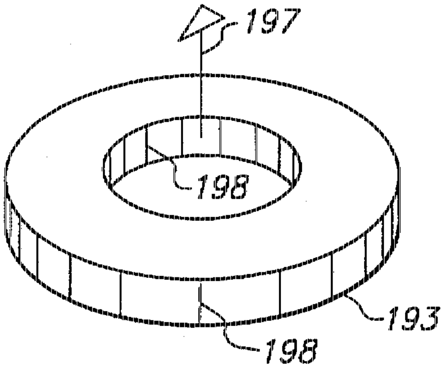

Accordingly, as seen in FIG. 14, each individual ring 193 is vacuum-coated with a conductive electrode (such as a gold-chromium mixture) 195 on either lateral side of the ring. The poling vector of the PZT sheet is reset by applying a very high voltage across the electrodes 195, on the order of 60- to 80-volts per mil of thickness of the PZT ring. In the preferred embodiment, rings are cut to be approximately $\frac{1}{2}\lambda_L$ in lateral (as opposed to radial) thickness. Once this step is performed, a new poling vector is created which is perpendicular to the geometry, as indicated by the reference arrow 197 of FIG. 14. The electrodes 195 are then removed from the lateral faces of the ring 193 by use of a lapstone or an equivalent etching process to produce a ring 193 that does not have any lateral electrode material, as indicated by FIG. 15.

Following electrode removal and resetting of the poling vector 197, new peripheral electrodes must be deposited on the radial surfaces 198 of the ring geometry to enable shear wave production upon application of the oscillation signal. Particle movement will be along the direction of the poling vector, with an oscillation signal motivating the rings to create sinusoidal particle motion and propagation of the shear waves.

Figure 16:
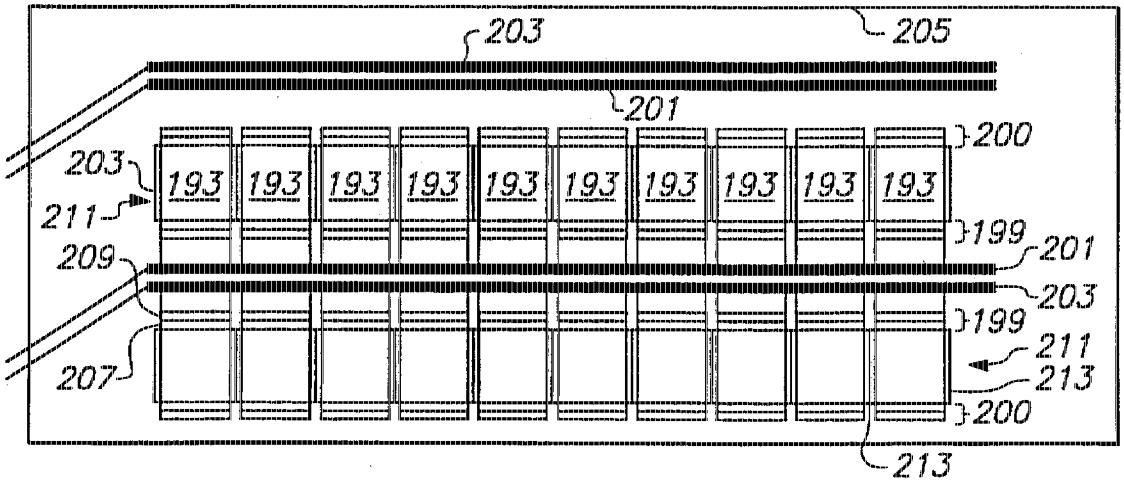

As indicated in FIG. 16, deposition of the new electrodes is preferably accomplished by stacking the ring transducers 193 together and by simultaneously vacuum-depositing the innermost and outermost electrodes 199 and 200 to radial edges of the ring transducers. First, the innermost electrodes 199 can be deposited using coated tungsten wires 201 and 203, which are passed into a vacuum chamber 205 and through the bores of the ring transducers. The wires 201 and 203 are then sequentially heated to deposit layers of electrode material in an evaporation procedure. Preferably, a first one 201 of the tungsten wires has been coated with chrome, and is used to apply a thin chrome layer 207 to improve adhesion of a principal conductor layer 209, preferably gold.

Prior to this procedure, lateral sides 211 of the ring transducers are deposited with a mask layer 213 so that no electrode material is deposited on them. A second one of the tungsten wires 203 is preferably coated with gold, and is heated to deposit the second, gold layer 209 to complete the electrode formation in the inner bore. Deposition of the outermost electrode 200 is similarly performed, with the transducers 193 rotated during the deposition procedure to promote uniform thickness in the electrodes. Following electrode deposition, the mask layer 213 is removed and the ring transducers 193 are ready for connection to the waveguide.

Figure 17:
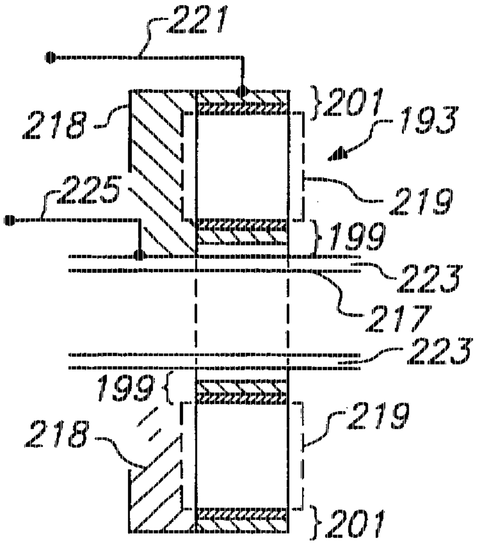
FIGS. 12–17 illustrate construction of a shear-wave transducer having ring geometry.

FIG. 17 illustrates electrical and physical installation of each ring transducer 193 upon a waveguide 217, and notably, the mask layer 213 has been removed as indicated by phantom lines 219 of FIG. 17. Prior to installation, each transducer ring 193 and the waveguide 217 are cleaned in soap and scrubbed using a small brush. The waveguide and rings are then rinsed in a series of ultrasonic baths, including sequential baths of methanol, acetone, and methanol. In each case, duration of the ultrasound bath is preferably at least 15 minutes. Each of the aforementioned parts are then dried in an oven and stored in dry conditions until the mounting procedure. For the mounting procedure, each transducer is coaxially fitted about the waveguide 217, such that the waveguide passes through the bore of all of the transducers. The epoxy is a 2-part mixture of premixed epoxy which is stored a low temperature (−40 Fahrenheit).

In general, a bonding fixture (not shown) is used to simultaneously mount all of the transducers and associated Teflon spacer rings 218. The epoxy is applied to both of the waveguide 217 and the inner bore of each transducer 193, and the fixture is then used to simultaneously load all of the transducers and spacer rings. The entire waveguide assembly is then put in an oven at 52 deg centigrade for a period of eight hours, to allow the epoxy to cure.

Electrical contact is made to each transducer 193 by connecting an electronic lead 221 to the outermost electrode 201 of each transducer 193, and by direct contact between each transducer's innermost electrode 199 and a thin conductive electrode 223 deposited on the periphery of the waveguide 217. A single lead 225 may be used to connect the thin conductive electrode 223 of the waveguide to a transformer center tap, as with center taps 81 or 127 (seen in FIGS. 6 and 8, respectively).

As can be seen from the above, the present invention provides an acoustic system that efficiently couples sound with a waveguide, and generates highly directional, intense sound. The present invention thereby provides utility to fields of measurement, medicine, communications, and other fields as well.

Various modifications of the exemplary embodiment described above will occur to those having skill in the art. For example, different transducer spacings could be employed, with the transducers excited by electrical phases of other than 180-degrees (e.g., a three-phase system could be implemented, using three electrical phases separated 120-degree). Alternatively, different transducers within an array could be made to generate different frequencies of ultrasound. Further still, many different transducer poling arrangements could be used. For example, transducer poling in the end-fire array could be alternated, to eliminate the need for a push-pull excitation source.

Having thus described an exemplary embodiment of the invention, it will be apparent that further alterations, modifications, and improvements will also occur to those skilled in the art. Further, it will be apparent that the present invention is not limited to the specific form of a system for coupling acoustic energy described above. Such alterations, modifications, and improvements, though not expressly described or mentioned above, are nonetheless intended and implied to be within the spirit and scope of the invention. Accordingly, the foregoing discussion is intended to be illustrative only; the invention is limited and defined only by the various following claims and equivalents thereto.

I claim:

1. An acoustic system, comprising:

an acoustic waveguide having a waveguide axis along which acoustic waves are capable of being longitudinally transmitted, and a waveguide periphery; and an acoustic shear wave transducer positioned to occupy at least two different positions at the periphery, the shear wave transducer adapted to transduce shear waves propagating in a plane substantially perpendicular to the waveguide axis;

wherein the at least two different positions are selected such that, when the transducer is driven, the transducer generates shear waves which propagate toward the waveguide axis and converge in mutual reinforcement, to thereby form a sweet spot within the acoustic waveguide, and the waveguide is effective to propagate corresponding longitudinal waves along the waveguide axis.

2. An acoustic system according to claim 1, wherein the shear wave transducer forms a substantially continuous transducer which extends around the waveguide periphery.

3. An acoustic system according to claim 2, wherein the acoustic waveguide has a substantially circular periphery in cross-section, and the shear wave transducer is a ring transducer positioned coaxial to the acoustic waveguide.

4. An acoustic system according to claim 1, wherein the shear wave transducer includes at least two separate transducer segments that are driven by a common oscillation signal.

5. An acoustic system according to claim 1, wherein the shear wave transducer includes at least two different pairs of segments, each pair of segments transducing shear waves of different frequency.

6. An acoustic system according to claim 1, wherein:

the acoustic system further comprises an excitation source that produces an electronic oscillation signal, the electronic oscillation signal operatively coupled to the shear wave transducer to drive the shear wave transducer; and the transducer generates acoustic shear waves in response to the oscillation signal, with corresponding longitudinal waves being propagated along the waveguide axis.

7. An acoustic system according to claim 6, wherein:

the system is embodied in an ultrasound angioplasty device, and the shear wave transducer is an ultrasound transducer;

the acoustic waveguide has two ends, including a first end proximate to the phased array and a second end; and the ultrasound angioplasty device includes an ultrasound catheter for invasive use in a living body, the ultrasound catheter coupled to the second end to receive ultrasound therefrom.

8. An acoustic system according to claim 1, wherein:

the transducer is adapted to detect acoustic shear waves in response to longitudinal waves being propagated along the waveguide axis at the predetermined frequency; and the acoustic system further comprises an electronic output from the shear wave transducer which is produced in response to acoustic waves detected by the shear wave transducer, the output indicating strength of longitudinal waves at a predetermined frequency corresponding to the transducer.

9. An acoustic system according to claim 8, wherein:

the acoustic waveguide includes a first end and a second end, the transducer positioned at the second end of the acoustic waveguide; and the system further comprises an acoustic generator capable of generating acoustic waves in response to an oscillation signal, the acoustic generator positioned at the first end of the acoustic waveguide, a feedback gain circuit adapted to receive the electronic output and produces the oscillation signal in response to the electronic output, and a dismay dependent upon the electronic output, the display thereby indicating change in the physical path that longitudinal waves travel along the waveguide axis.

10. In an acoustic delivery system that includes an excitation source, an acoustic generator that the excitation source causes to generate acoustic energy, and a waveguide that delivers acoustic waves from the generator to a remote location along a waveguide transmission axis, the improvement comprising:

at least two shear wave transducers of the generator, positioned at different points along the waveguide axis, each transducer having a shear wave transmission plane which is perpendicular to the waveguide transmission axis, each transducer configured to generate shear waves of a predetermined frequency;

wherein the different points of the shear wave transducers are selected to cause constructive reinforcement of the acoustic waves when the transducers are driven at the predetermined frequency.

11. An improvement according to claim 10, further comprising:

a phase delay coupled between at least one transducer and the excitation source, to thereby cause relative delay in production of shear waves between two transducers, the phase delay selected to correspond to a spatial interval between the two transducers to cause the two transducers to mutually reinforce propagation of a longitudinal wave along the transmission axis.

12. An improvement according to claim 10, wherein said improvement is embodied in an ultrasound angioplasty system having a catheter-mounted bulbous termination that delivers vibrational energy to a stenosed region of a blood vessel, the termination coupled to the waveguide at the remote location, the improvement further comprising:

using ultrasound transducers to produce ultrasound shear waves; and utilizing a waveguide to couple the ultrasound to the termination;

wherein the termination responsively delivers vibrational energy to the stenosed region of the blood vessel.

13. An improvement according to claim 10, wherein said improvement further comprises:

using the waveguide to couple ultrasound to the remote location; and using a ring transducer for each shear wave transducer, each ring transducer having a bore which receives the waveguide in a manner such that the ring transducer fits around a periphery of the waveguide.

14. An improvement according to claim 13, wherein said improvement further comprises:

using ring transducers that are circularly symmetric about the waveguide.

15. A method of transducing acoustic energy using a waveguide having a waveguide axis along which acoustic waves are longitudinally transmitted, a plurality of shear wave transducers having an associated acoustic frequency, and electrical couplings of the transducers, which carry electric signals corresponding to the particular acoustic frequency, comprising:

positioning the shear wave transducers proximate to the waveguide and along it such that the transducers transduce shear waves which propagate along a shear wave plane perpendicular to the waveguide axis;

spacing the plurality of transducers along the waveguide axis at fractions of a wavelength (corresponding to the particular acoustic frequency); and equalizing relative phases of the plurality of transducers by providing phase lags to them;

wherein the shear wave transducers are spaced at intervals relative to the phase lags such that the shear wave transducers collectively form a phased array tuned to the particular acoustic frequency, to thereby transduce the acoustic energy.

16. A method according to claim 15, wherein the waveguide includes an acoustic waveguide and the plurality includes at least five circularly-symmetric ring transducers in parallel, spaced apart relation along the waveguide axis around the periphery of the acoustic waveguide, further comprising:

generating shear waves in a symmetric, radially-inward manner within the acoustic waveguide, such that shear waves are maximized in amplitude substantially at a center axis of the acoustic waveguide, and are transmitted longitudinally substantially on the center axis.

17. A method according to claim 15, wherein the ring transducers each include two pairs of transducer segments, each driven by different oscillation signals, the method further comprising:

providing each of the different oscillation signals to a pair of segments; and generating at least two different shear waves to concurrently propagate two independent longitudinal waves along the waveguide axis.

18. A method according to claim 15, further comprising using the phased array as a sonic detector and producing an electronic output representing magnitude of sound in the waveguide at the particular acoustic frequency.

19. A method according to claim 18, further comprising applying gain to the electronic output to form an amplified output, and applying the amplified output to an ultrasound generator to form a resonant ultrasound system.

* * * * *